(12) United States Patent
Tallberg

(10) Patent No.: US 8,703,211 B2
(45) Date of Patent: Apr. 22, 2014

(54) AGENT AND METHOD FOR TREATING CANCER COMPRISING STRONTIUM, AMINO ACID(S) AND MINERAL AGENT(S)

(75) Inventor: Thomas Tallberg, Helsinki (FI)

(73) Assignee: Oy Neurofood AB, Espoo (FI)

(*) Notice: Subject to any disclaimer, the term of this patent is extended or adjusted under 35 U.S.C. 154(b) by 285 days.

(21) Appl. No.: 12/626,980

(22) Filed: Nov. 30, 2009

(65) Prior Publication Data

US 2010/0074968 A1    Mar. 25, 2010

Related U.S. Application Data

(62) Division of application No. 10/575,752, filed as application No. PCT/FI2004/000618 on Oct. 15, 2004, now abandoned.

(30) Foreign Application Priority Data

Oct. 17, 2003   (EP) .................................... 03103850

(51) Int. Cl.
| | | |
|---|---|---|
| *A61K 33/00* | (2006.01) | |
| *A61K 33/14* | (2006.01) | |
| *A61K 31/197* | (2006.01) | |
| *A61K 31/198* | (2006.01) | |
| *A61K 45/00* | (2006.01) | |
| *A61P 35/00* | (2006.01) | |

(52) U.S. Cl.
USPC ........... 424/722; 424/522; 424/570; 424/617; 424/646; 424/650; 424/655; 424/677; 426/72; 514/561; 514/563; 514/565

(58) Field of Classification Search
None
See application file for complete search history.

(56) References Cited

U.S. PATENT DOCUMENTS

| 5,851,556 A | 12/1998 | Breton et al. |
| 5,866,168 A | 2/1999 | De Lacharriere et al. |

FOREIGN PATENT DOCUMENTS

| EP | 0 366 869 | 5/1990 |
| EP | 0 737 471 | 10/1996 |
| GB | 602029 | 5/1948 |
| WO | 95/33493 | 12/1995 |
| WO | 97/40889 | 11/1997 |
| WO | 00/07607 | 2/2000 |
| WO | 01/15552 | 3/2001 |
| WO | 01/41822 | 6/2001 |
| WO | 01/73792 | 10/2001 |
| WO | 00/07607 | 2/2002 |
| WO | 03/028742 | 4/2003 |
| WO | 03/075957 | 9/2003 |

OTHER PUBLICATIONS

Narkia, Tallberg's cancer bioimmunotherapy—a nontoxic cancer treatment, Sci.Med.Diseases.Cancer (1999).*
Derwent Abstract of CN 1 113 720 dated Dec. 27, 1995 XP-002273246.
Curzon, M. E. J. et al. "Effect of Using Different Strontium Salts on Dental Caries in the Rat" *Caries Research* (1981) vol. 15, pp. 296-301.
Database WPI Week 199739 Derwent Publications Ltd., London, GB:AN 1997-416121 XP002273246 & CN 1113720A (Zhicheng Sci & Tech Ind Co Yunnan) Dec. 27, 1995.
Curzon, M. E .J., et al. "Effect of Using Different Strontium Salts on Dental Caries in the Rat." Caries Res. 15 (1981) pp. 296-301.
WPI/Thomson Derwent Abstract AN 1997-165937 & CN 1091925 (Peng J), DW 199716, Sep. 14, 1994.
WPI/Thomson Derwent Abstract AN 1995-179396 & CN1082845 (Yan H), DW 199524, Mar. 2, 1994.
Sips, et al. Br. J. Clin. Pharmacol. vol. 41, pp. 543-549 (1996).
Micuccii, The Ohio State University Extension Fact Sheet, ZINC, HYG-5560-06, pp. 1-4 [online], [retrieved on Aug. 13, 2009]. Retrieved from the Internet <url:http://ohioline.osu.edu/hygfact/5000/pdf/5560.pdf>.

* cited by examiner

*Primary Examiner* — Abigail Fisher
*Assistant Examiner* — Frank Choi
(74) *Attorney, Agent, or Firm* — Ladas & Parry LLP

(57) ABSTRACT

The invention relates to the treatment and prophylaxis of cancer. In particular, the invention relates to a pharmaceutical agent comprising strontium, amino acid(s) and mineral element(s), and its use in the preparation of an agent useful for the treatment and prophylaxis of cancer. The invention also relates to a method for treatment and prophylaxis of cancer.

3 Claims, No Drawings

AGENT AND METHOD FOR TREATING CANCER COMPRISING STRONTIUM, AMINO ACID(S) AND MINERAL AGENT(S)

This application is a divisional of application Ser. No. 10/575,752 filed on Apr. 12, 2006 now abandoned, which is a 371 of PCT/FI2004/000618 filed on Oct. 15, 2004, which designated the U.S., claims the benefit thereof and incorporates the same by reference.

The invention relates to the treatment and prophylaxis of cancer. In particular, the invention relates to a pharmaceutical agent comprising strontium, amino acid(s) and mineral element(s) and its use in the preparation of an agent useful for the treatment and prophylaxis of cancer. The invention also relates to a method for treatment and prophylaxis of cancer.

BACKGROUND OF THE INVENTION

Cancer is one of the most widespread and severe diseases with huge implications both in terms of human suffering and costs for national health care systems and individual patients. Among the cancer forms, the incidence of e.g. prostate cancer (CaP) and melanoma is steadily increasing around the world.

Carcinoma of the prostate is still potentially an incurable age-linked disease of unknown etiology. Descriptive epidemiology suggests that the probable causes of CaP are determined rather on environmental than genetic factors, and that dietary habits have a pronounced effect on prostate cancer incidence. "Latent disease" may actually be a result of dietary habits and life style.

Today, the standard treatment for prostate cancer involves drastic decrease in the patient's testosterone level. Earlier, this was carried out as an invasive operative treatment, in essence a castration operation. Nowadays the treatment usually is based on the administration of biologically active peptides, so called LHRH analogues, which via the pituitary gland inhibit the patient's androgen and testosterone production. Both treatments lead to a sharp decrease in the testosterone level, but the clinically positive result is only temporary, and a therapeutic effect is usually observed only for about 1-2 years. As time goes on all patients develop a hormone refractory state, during which the dramatically reduced androgen and testosterone levels cannot prevent recurrence of the disease. The standard therapies involve severe side effects coupled with deterioration of the life-quality of the cancer patient and his family. Furthermore, the treatments are very expensive, both for the national health care system and for the patient himself, and nevertheless, cure cannot be guaranteed.

Therefore, there exists a great demand for improved methods for treating cancer, which methods should be both less expensive and better tolerated by the patient.

SHORT DESCRIPTION OF THE INVENTION

The present invention aims at providing such an improved agent and method for treating cancer.

The invention resides in the utilization of the beneficial effects of strontium, which have been observed in connection with the present invention.

The invention hence relates to a pharmaceutical agent comprising strontium (Sr) in combination with (other) specific dietary supplements, such as amino acids, mineral elements and/or vitamins.

In accordance with a preferred embodiment of the present invention, strontium is utilized in the form of strontium ions. Said ions can be provided by using strontium in the form of a strontium salt, e.g. strontium chloride or strontium oxide.

In one especially preferred embodiment, the invention relates to a pharmaceutical agent comprising strontium, at least one amino acid selected from the group consisting of arginine (Arg), serine (Ser), asparagine (Asp), glycine (Gly), glutamine (Glu), and at least one mineral element selected from the group consisting of chromium (Cr), tin (Sn), vanadium (V) and wolfram (W).

The pharmaceutical agent can be in the form of a food additive or a food ingredient. Dairy products, in particular yoghurt, are regarded as preferred.

The invention also relates to the use of the pharmaceutical agent including strontium for the manufacture of an agent for treatment or prophylaxis of cancer.

Further, the invention relates to a method for treatment or prophylaxis of cancer, said method comprising the administration to an individual in need of such treatment the pharmaceutical agent including strontium in an amount sufficient to achieve the desired effect. In connection with the present invention, the treatment and/or prophylaxis also include delaying or prevention of recurrence of the disease.

In particular, the cancer form is an adenocarcinoma, such as prostate cancer or renal carcinoma, or melanoma.

DETAILED DESCRIPTION OF THE INVENTION

In connection with the present invention, the etiology and prognostic traits in patients suffering from cancer of the prostate gland (CaP) was elucidated. The aim was to medically restore, in an active but non-invasive way, the normal metabolic balance and mitochondrial control of oncogen transcription in CaP.

During the study a wide range of changes in hormonal and biomodulating factors were measured and followed for years in selected patients during different stages of prostate cancer, while they were receiving various forms of therapy. The biological and pathophysiological responses were followed-up for over twenty years in some cases.

The treatment successfully used according to the present invention is based on the administration of strontium (Sr) in combination with amino acid(s) and trace element(s).

The results obtained in connection with the present invention clearly show that a daily intake of strontium chloride leads to a significant increase in the serum prolactin (PRL) level. When healthy individuals were given 7 mg strontium chloride per day, the PRL level increased within two weeks 50-80% from a normal base value. Simultaneously, the serum dihydroepiandrosteron sulphate (DHEAS) level decreased, although the serum dihydroepiandrosteron (DHEA) level can show an increase in value in the same individual (table±4).

It has also been found that the effect of the novel strontium treatment, as well as standard LHRH treatment, can be significantly improved by also using some specific natural dietary supplements. These supplements include natural amino acids, such as arginine (Arg), serine (Ser), asparagine (Asp), glycine (Gly), glutamine (Glu), and lysine (Lys), mineral salts, such as chromium, tin, vanadium and wolfram, and vitamins, such as A, B, C, D, E, K, folic acid and lycopene, as well as neurogenic lipids.

The supplements are used in amounts sufficient to achieve the desired health promoting effect. As will be readily understood by a physician, the amounts will vary depending on the individual and his health status, as well as other factors such as weight, age, nutrition, stress and environmental factors, etc. Examples of suitable amounts include, but are not limited to, about 2-5 g per day of the specific amino acids mentioned, and 0.5-6, preferably 1-3 mg per day of the trace element salts. The vitamins are used in small, well-established physiological amounts. The dosage of lycopene can, for instance, be about 2 mg per day.

Neurogenic lipids can be obtained and administered e.g. in the form of brain, purchased and canned by Neurofood Ltd., Finland. The daily intake can correspond for instance to about 50 g brain.

In accordance with the present invention, the components of the agent can be administered individually. They can also be administered together, as a combined preparation. The clinically active—combined formulation can also be administered as such or together with a conventional foodstuff. The formulation can be prepared e.g. as pre-packed pulvers. Mixing the formulation, or individual pulverized ingredients, in the patients morning yoghurt, as described below, has been found to be preferred; for the consumer it is easy to enjoy in connection with the morning breakfast or as a snack between meals.

A preferred combination according to the invention can comprise the following (calculated as daily intake):

| | |
|---|---|
| Strontium chloride | 0.1-7 mg |
| L-amino acids | 2-5 g |
| (Arg, Asp, Glu, Gly, Lys, Ser) | |
| mineral salts | 1-7 mg |
| (chromium chloride, tin chloride, vanadium as sodium salt, wolfram as sodium salt) | |
| Vitamins | |
| (A, B, C, D, E, K, folic acid, lycopene) | |

Three examples of supportive dietary measures, or dietary bio-modulation schedules, are given above. The schedules are given by way of exemplification. After the publication of the present document, a person skilled in the art will be able to make variations and modifications thereof, having the same beneficial effects as described above.

Dietary Bio-Modulation Schedule for Prostate Carcinoma

Supportive Dietary Measures:
1. Oral administration of each (2-5 g/day) of respective L-amino acids: Arg, Asp, Glu, Gly, Lys and Ser in connection with meals
2. Essential trace-element salts prescribed orally as biologically active ions, at dose levels of some milligrams (1-3 mg/day): Chromium ($CrCl_2.6H_2O$) 6 mg (=1.17 mg Cr), Tin ($SnCl_4.5H_2O$) 4 mg (=1.35 mg Sn), Strontium ($SrCl_2$) 0.1-7 mg (0.1-3 mg Sr), Vanadine ($Na_2VO_4.4H_2O$), 6 mg (=2.5 mg V), Wolfram ($Na_2WO_4.2H_2O$), 4 mg (=2.3 mg W)
3. Small physiologic amounts of vitamins: A, B, C, D, E, K, folic acid and lycopene
4. To improve lymphopoiesis and the immune defense of patients a diet containing prionfree neurogenic lipids (equivalent to approx. 50 g of brain) was recommended, (purchased and canned by Neurofood Ltd. Finland)
5. All these dietary ingredients can be mixed together in yoghurt, forming a daily ration, using pre-packed pulvers
6. Dose-levels are adjusted based on clinical response as measured, and correlated to the patient's body weight.

Dietary Bio-Modulation Schedule for Renal Cell Carcinoma

Supportive Dietary Measures Started Prior to Surgery:
1. Oral administration (of approximately 5 g/day) of L-amino acids: Ala, Arg, Asp, Lys and Ser
2. Essential trace-element salts prescribed orally as biologically active ions: Cr, Mo, Se, Sn, Sr, V as mg's/day and Mn (manganese glycerophosphate $C_3H_7MnO_6P.H_2O$) as 100 mg/day
3. Physiological doses of vitamins: A, B, C, D, E, K and folic acid 2 mg/day
4. Diet containing neurogenic lipids such as ice-cream (cooked brain from healthy pigs, available as canned "functional" food)
5. Patients should avoid foods and vitamin preparations rich in zinc (possibly a growth factor for renal adenocarcinoma cells)

Dietary Bio-Modulation Schedule for Melanoma

Supportive Dietary Measures Started at Diagnosis of Melanoma:
1. Oral administration (of approximately 5 g/day) of L-amino acids: Ala, Asp, Ile, Lys and Gly, Glu together with a small dose of aspirin (50-100 mg/day)
2. Essential trace-elements administered orally as biologically active salts: Cr, Mg, Se, Sn, Sr, V, W ($Na_2WO_4.2H_2O$) as mg's/day
3. Physiological doses of vitamins: A, B, C, D, E, K and folic acid 2 mg/day
4. Repeated vaccinations against influenza A and B strains
5. Diet containing neurogenic lipids such as ice-cream (cooked brain from healthy pigs, available as canned food, Neurofood).

The schedules above show that the composition of the pharmaceutical agent can vary depending on type of cancer, among other things. For the treatment of prostate cancer, the agent should include, in particular, strontium and serine, vanadium being the preferred trace element. Also arginine is regarded as a preferred component. For renal cell carcinoma, the main components of the agent are strontium, arginine and vanadium, and for the treatment of melanoma, isoleucin and strontium have been shown to have excellent effects, in combination with one of more of the trace elements Cr, Se, Sn, V and W.

No side effects have been observed in connection with the intake of the pharmaceutical agent, not even in the case where the patient (P1) had used the combined dietary supplement and strontium for more than 12 years.

Strontium has not previously been reported to have therapeutic effects. Radioactive Strontium[89] has, however, earlier been used to scan bone-metastases. Sr homes into the metastases, although only about 10% of the i.v. dose (up to 80 mg $SrCl_2$) may be radioactive $^{89}$Sr it is sufficient for the localization. However, repeated trials to localize bone-metastases were hampered since the scanning became unreliable. Probably the excess of non-radioactive Sr injected was blocking the cell receptors. Therefore, presently technetium is used for this diagnostic purpose. No harmful therapeutic side effects of the long-lasting use of strontium for diagnostic purposes have been reported. In connection with the present invention, radioactive strontium need not be used.

Treatment of cancer by bio-modulation using strontium in combination with other supplementary factors as described above offers a unique non-toxic physiological method for the treatment and prophylaxis of cancer. Although the results presented in the examples mainly relate to patients suffering from prostate cancer, which is a adenocarcinoma, preliminary results obtained in studies involving renal cancer and melanoma patients give clear indications that the treatment is effective also on other cancer forms.

The most important clinical parameter seems to be the significantly decreased DHEAS level. Hence, without wishing to be bound by any theory, the inventor believes that the strontium intake may block the sulfonation of the dihydroepiandrosteron (DHEA).

After dietary supplementation, comprising the natural amino acids (at a dose of approx. 3-5 g/d): Arg, Asp, Glu, Gly, Lys, and especially Ser, together with the trace-element salts; Cr, Sn, Sr and W, sometimes also Zn (in mgs'/day), Ca and Mn, a positive effect was observed. In sharp contrast, trials with specific immunotherapy using autologous vaccines decreased the PSA levels only for a limited time but did not arrest CaP.

On the basis of the research results, it is believed that standard hormone treatment leads to a feed-back reaction mediated by the third cell layer in the adrenal gland, zona reticularis (ZR). The biological cycle that can reduce the patient's prostate specific antigen (PSA), involves physiologically cooperation between four organs, the ZR of the adrenal gland, the pituitary gland through the hypothalamus, the testicles, and the healthy cells in the prostate gland. The ZR cells in the adrenal gland are believed to produce a biological factor inducing a decrease in a previously increased PSA level, which is seen as a sign of inhibition of prostate cancer cell growth. The inventor has found that prolonged therapeutic effect can be achieved by carrying out LHRH treatment intermittently using a short cycle, i.e. repeating the treatment only when the patient's PSA and testosterone levels again begin to raise. This can effectively hinder the development of a hormone refractory state.

The ZR cells seem to produce at least two unknown endocrine factors which cause an increase in FSH- and/or PRL-levels. Elevation of these hormone reactions signal a positive prognostic sign, especially coupled with a decreased DHEAS. The stimulation of FSH and PRL appear to form an essential part in the cycle preserving the normal gene transcription of prostate cells, probably also involved in the mitochondrial regulation, which can retract oncogen transcription in CaP cells.

Androgen ablation therapy does not seem to promote inhibition of crucial enzyme reactions, especially the sulphonation of DHEA to DHEAS. A decreasing level of DHEAS seems to constitute an important part of the biological reactions arresting malignant cell growth in the prostate gland. The 5a-reductase level was found to decrease in certain patients, but the enzyme does not seem to arrest CaP, and does not seem to be as important a prognostic factor as the depressed sulphonation of DHEA or its isomer.

In the following, the invention will be described in greater detail by means of examples. These examples are only intended to illustrate the invention, and should not be construed as restricting its scope in any way. The studies described were carried out with informed consent from the patients that were offered the dietary supplementation schedule with the aim of causing a therapeutic bio-modulation.

EXAMPLE 1

Orchiectomy Combined with Dietary Bio-Modulation

A male patient (P1) suffering from prostate cancer was initially orchiectomized 13 years ago. In 1990, when multiple bone-metastases had developed, and the PSA value was 360 µg/L, he was prescribed supportive dietary measures. In addition to the dietary biomodulating components prescribed (see Table 1), the patient ingested a daily amount of 7 mg of strontium oxide, contained in birch ash that he prepared at home and was taking continuously at a dose of about 8 g per day. His bone-pain subsided in 6 months following the beginning of the treatment, the bone-metastases disappeared after four years, and now in year 2003 the patient is in excellent clinical condition. The serum dihydroepiandrosteron sulphate (DHEAS) level is below the detectable limit of 0.8, the dihydroepiandrosteron (DHEA) value is below 2.0, and his prolactin (PRL) value is normal, about 97 mU/l. The follicle stimulating hormone (FSH) level is increased, about 48 IU/l. This value increases in all castrated patients that react positively on the drastic and provocative decrease in the testosteron level resulting from the surgical operation. The laboratory pattern is presented in Table 2.

TABLE 1

DIETARY BIO-MODULATION SCHEDULE

Supportive dietary measures:

1. Oral administration of each (2-5 g/day) of respective L-amino acids: Arg, Asp, Glu, Gly, Lys and Ser in connection with meals. The amino acids are manufactured by Degussa Ag, Germany.
2. Essential trace-element salts prescribed orally as biologically active ions, at dose levels of some milligrams (1-3 mg/day); Chromium ($CrCl_2 \cdot 6H_2O$) 6 mg (=1.17 mg Cr), Tin ($SnCl_4 \cdot 5H_2O$) 4 mg (=1.35 mg Sn), Strontium ($SrCl_2$) 0.1-7 mg (0.1-3 mg Sr), Vanadine ($Na_2VO_4 \cdot 4 H_2O$), 6 mg (=2.5 mg V), Wolfram ($Na_2WO_4 \cdot 2 H_2O$), 4 mg (=2.3 mg W)
3. Small physiologic amounts of vitamins: A, B, C, D, E, K, folic acid and lycopene.
4. To improve lymphopoiesis and the immune defense of patients a diet containing prionfree neurogenic lipids (equivalent to approx. 50 g of brain) was recommended, (purchased and canned by Neurofood Ltd. Finland)
5. All these dietary ingredients can be mixed together in yoghurt, forming a daily ration, using pre-packed pulvers.
6. Dose-levels are adjusted based on clinical response as measured, and correlated to the patient's body weight.

TABLE 2

LABORATORY PATTERN FOR PATIENT P1

| | FSH IU/L 1-7#9 | LH IU/L 2.5-12 | PRL mU/L 50-300 | DHEA nmol/L 3.0-17.0 | DHEAS µmol/L 0.0-8.0 | Testost nmol/l 9-38 | Inhibin pg/ml ~60 pg/ml | Activin pg/ml ~500 pg/ml | S-Ferrit µg/L 16-253 | SHBG nmol/L 15-50 | PSA µg/L <4.0 |
|---|---|---|---|---|---|---|---|---|---|---|---|
| No. 1 | 67-30 | 37-16 | 15-95 | <2.0 | <0.8 | 1.0 | <7.8 | 330-500 | 109-99 | 58-61 | <0.1 |

EXAMPLE 2

Patients with Initially Increased FSH and Prolactin Levels

The example concerns patients with confirmed diagnosis for CaP, based on needle biopsies, and having increased FSH levels. The patients are numbered as patients 6-9 in Table 3. The patients FSH levels varied from 19-70 IU/L, as compared to the normal value 9 IU/L. Their PSA levels were usually 20-30 μg/ml, however, the disease can be stable for years without any treatment or following only dietary measures. The LH-level may be slightly elevated or depressed without affecting the prognosis. DHEA and DHEAS levels were normal or slightly depressed but as long as the FSH is elevated, the prognosis is fair.

One of the patients (No. 8) had needle biopsies taken every year, because his PSA was 30 μg/L, for five years without a positive diagnosis for CaP. Finally a biopsy was found showing an aggressive Gleason score of 8. The protracted case history was seen to be due to an iatrogenically high FSH-level, of up to 70 μg/L. His disease reacted very well to a combined, intermittent LHRH analogue hormone therapy, in synergy with the dietary measures described above (Table 3).

Patients showing initially elevated, and increasing PRL-levels have been followed for years, in deferred treatment, without showing signs of progressive disease. The results for one patient, No 9, are also given in table 3. Prolactin seems to be one of the factors involved in preserving normal prostate cell function. PRL increases also when ZR-extracts are ingested, prepared by micromanipulation of ZR cells from castrated pigs. Ingestion of strontium (in mg's) was found to cause a PRL increase in healthy persons (>50%) coinciding with a decrease in his DHEAS (~40%), a reaction pattern usually considered as a favourable prognostic sign.

TABLE 4

EFFECT OF STRONTIUM ON SOME HORMONE LEVELS

| | serum DHEA nmol/L 3-7 | DHEAS μmol/L <8 | PRL mU/L 70-300 | FSH IU/L 1-9 | PSA μg/L <4.5 |
|---|---|---|---|---|---|
| Base value for healthy individual | 3.4 | 3.1 | 201 | 15 | 0.5 |
| After Sr (7 mg, 14 days), with P0 | 9.8 | 2.3 | 389 | 13 | 0.4 |
| P0 without Sr for three weeks | 3.6 | 2.7 | 337 | 11 | 0.4 |
| Patient P1 Sr + full dietary supplementation | | <0.8 | 97 | 48 | <0.1 |
| Patient P2 | | <0.8 | 852 | | 12.6 |
| Patient P3 ± | 4.3 | 2.5 | 568 | 12 | 12.7 |
| Patient P4 ± | 2.4 | <0.8 | 1879 | 13 | 24.0 |

The results clearly show the significant decrease in the DHEAS level.

The invention claimed is:

1. A method for the treatment of prostate cancer which consists of administering to a subject in need thereof one or more neurogenic lipids and a dietary supplement which consists of strontium in the form of a strontium salt, one or more one amino acids selected from the group consisting of arginine, serine, asparagine, glycine, glutamine, lysine, one or more mineral element salts selected from the group consisting of chromium, tin, vanadium and wolfram salts, and one or more vitamins.

2. A method of treatment of prostate cancer according to claim 1, characterized in that strontium is present in the dietary supplement in the form of strontium chloride.

TABLE 3

LABORATORY PATTERN FOR PATIENTS 6-9

| | FSH IU/L 1-7#9 | LH IU/L 2.5-12 | PRL mU/L 50-300 | DHEA nmol/L 3.0-17.0 | DHEAS μmol/L 0.0-8.0 | Testost nmol/l 9-38 | Inhibin pg/ml ~60 pg/ml | Activin pg/ml ~500 pg/ml | S-Ferrit μg/L 16-253 | SHBG nmol/L 15-50 | PSA μg/L <4.0 |
|---|---|---|---|---|---|---|---|---|---|---|---|
| No. 6 | 18.6 | 13.4 | 242 | 6.3 | 3.9 | 7.6 | 66 | 790 | 133 | 27 | 14.4 |
| | 18.0 | 12.8 | 241 | 4.0 | 3.3 | | 83 | 550 | 86 | | 13.0 |
| No. 7 | 27.2 | 11.8 | 144 | 7.8 | 5.0 | 16 | 73 | 430 | 38 | 49 | <0.3 |
| | 27.0 | 11.0 | 162 | 5.3 | 4.2 | 16 | | | 34 | 49 | <0.4 |
| No. 8 | 75.0 | 33.0 | 224 | 20.9 | 2.3 | 6.7 | (TSH 9.8) | | 20 | 38 | 29.8 |
| | 13.0 | 0.1 | 122 | 2.9 | 1.5 | 10.0 | | | 50 | 34 | 2.8 |
| No. 9 | 2.3 | 3.9 | 392 | 3.4 | 1.1 | 12.9 | 187 | 92 | 55 | 46 | <1.0 |
| | 2.1 | 2.4 | 566 | 2.8-2.4 < 2 | <0.8 | 9.8-8.9 | | | 44 | 37 | 1.7/29% |

EXAMPLE 3

The Effect of Strontium Intake on Selected Physiological Reactions

The effect of strontium intake on selected physiological reactions was evaluated by administering strontium alone or together with the full dietary support program described in table 1 to four prostate cancer patients, P1-P4, and to one healthy individual. The results are shown in table 4, which also gives the normal values for the measured hormones.

3. A method of treatment of prostate cancer according to claim 1, characterized in that the dietary supplement consists of 0.1-7 mg strontium chloride, at least one L-amino acid selected from the group consisting of arginine, serine, asparagine, glycine, glutamine, lysine, in an amount of 2-5 g of each of the chosen amino acids, at least one mineral element salt selected from the group consisting of chromium, tin, vanadium and wolfram salts, and one or more vitamins, in an amount of 1-3 mg of each of the chosen mineral element salts, the amounts being calculated as daily intake.

* * * * *